United States Patent [19]
Østensen

[11] Patent Number: 6,054,118
[45] Date of Patent: Apr. 25, 2000

[54] CONTRAST AGENTS COMPRISING TWO TYPES OF GAS-CONTAINING MICROPARTICLES

[75] Inventor: Jonny Østensen, Oslo, Norway

[73] Assignee: Nycomed Imaging AS, Oslo, Nauru

[21] Appl. No.: 09/078,274

[22] Filed: May 14, 1998

Related U.S. Application Data

[63] Continuation of application No. PCT/GB98/00189, Jan. 22, 1998
[60] Provisional application No. 60/046,712, Nov. 16, 1997.

[30] Foreign Application Priority Data

Jan. 22, 1997 [GB] United Kingdom .................... 9701237

[51] Int. Cl.$^7$ ........................................................ A61B 8/13
[52] U.S. Cl. .............................................................. 424/9.52
[58] Field of Search ............................. 424/9.52; 600/458

[56] References Cited

U.S. PATENT DOCUMENTS

| | | | |
|---|---|---|---|
| 5,147,631 | 9/1992 | Glajch et al. | 424/9.52 |
| 5,393,524 | 2/1995 | Quay | 424/9.52 |
| 5,599,523 | 2/1997 | Beller et al. | 424/9.52 |
| 5,772,984 | 6/1998 | Berg et al. | 424/9.52 |

FOREIGN PATENT DOCUMENTS 96 07434   3/1996   WIPO .

OTHER PUBLICATIONS

D.L. Miller, *Ultrasonics*, "Ultrasonic detection of resonant cavitation bubbles in a flow tube by their second–harmonic emissions", 19:217–224 (1981).

Maruyama et al., Proc. Natl. Acad. Sci. U.S.A., vol. 87, No. 15, pp. 5744–5748 (1990).

Schneider et al., Investigative Radiology, vol. 30, No. 8, pp. 451–457 (1995).

Alexander et al., Magnetic Resonance in Medicine, vol. 35, No. 6, pp. 801–806 (1996).

Porter et al., 68$^{th}$ Scientific Session of the American Heart Association, Anahein, CA, Nov. 13–16, 1995 Circulation, vol. 92, No. 8 Suppl., p. 1463 (1995).

Jong, IEEE Engineering in Medicine and Biology Magazine, vol. 16, No. 6, pp. 72–82 (1996).

Porter et al., "A Sub–Therapeutic Quantity of Aminophylline Mixed with Perfluoropropane–Enhanced Sonicated Dextrose Albumin Produces Significantly Improved Myocardial Ultrasound Opacification Following Intravenous Injection", Circulation, vol. 90, No. 4 part 2, p. 1556 (1994).

Ophir et al., Ultrasound in Medicine and Biology, vol. 15, No. 4, pp. 319–333 (1989).

*Primary Examiner*—Gary E. Hollinden
*Attorney, Agent, or Firm*—Bacon & Thomas

[57] ABSTRACT

Ultrasound contrast agents comprising two or more types of gas-containing microparticles which differ in their susceptibility to ultrasonic pressure. Microparticle types having relatively low susceptibility to ultrasonic pressure provide a response to high acoustic energy in the near field where microparticle types with relatively high susceptibility tend to be inactivated through destruction. More highly susceptible microparticle types are effective in the lower acoustic energy environment of the far field, where lower susceptibility microparticle types will tend to exhibit little interaction.

11 Claims, No Drawings

CONTRAST AGENTS COMPRISING TWO TYPES OF GAS-CONTAINING MICROPARTICLES

This application is a continuation of international application PCT/GB98/00189 filed Jan. 22, 1998. Benefit of the filing date of provisional application Ser. No. 60/046,712 filed Nov. 16, 1997, is claimed under 35 U.S.C. 119(e).

This invention relates to ultrasound imaging, more particularly to novel contrast agent compositions and preparations comprising at least two types of gas-containing microparticles and to their preparation and use.

It is well know that ultrasound imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas microbubbles and encapsulated gases or liquids. The use of gas-containing and gas-generating systems has attracted particular interest, since the low density and ease of compressibility of gas present or generated in such systems ensure particularly efficient backscatter of ultrasound.

Initial studies involving free gas microbubbles generated in vivo by intracardiac injection of physiologically acceptable substances demonstrated the potential efficiency of such microbubbles as contrast agents in echography; such techniques proved to be severely limited in practice, however, by the very short lifetime of the microbubbles in the body. Much interest has accordingly been shown in methods of stabilising gas microbubbles for echocardiography and other ultrasound studies, for example using emulsifiers, thickeners or sugars, or by entraining or encapsulating the gas or a precursor therefor in a variety of systems, e.g. as porous gas-containing microparticles or as encapsulated gas microbubbles, for example using encapsulating materials such as proteins, polymers or film-forming surfactants such as phospholipids.

Recent work in this area has shown a trend towards minimising the thickness of any encapsulating material, it having been recognised (see e.g. WO-A-9503835) that thick encapsulating shells reduce the compressibility and thus the echogenicity of the microbubbles. It is suggest in U.S. Pat. No. 5,393,524 that certain biocompatible fluorocarbons may be used in the form of free gas microbubbles by virtue of their persistence relative to air in aqueous media such as blood. Contrast agents comprising encapsulated or otherwise stabilised dispersions of substantially water-insoluble fluorinated gases have also been proposed—see, for example, the disclosure of WO-A-9501187 regarding protein microspheres containing water-insoluble gases such as perfluoropropane and the description of BR1, a phospholipid-stabilised dispersion of sulphur hexafluoride-filled microbubbles, in Investigative Radiology 30(8), pp. 451–457.

Whilst such contrast agents tend to exhibit a higher echogenic response and lower attenuation than contrast agents having thicker and/or more rigid encapsulating shells, they do in consequence suffer the disadvantage that they have relatively low resistance to high acoustic pressure, for example such as may be encountered in the near field in close proximity to the ultrasound transducer. Imaging at diagnostically useful ultrasound intensities may therefore lead to substantial destruction of the contrast agent in the near field.

It has been proposed to overcome this problem by imaging at low acoustic field strengths or by using intermittent ultrasound pulses, for example triggered by every tenth, twentieth or thirtieth cardiac cycle. However, this may prevent continuous imaging with good opacification in the near field and/or give rise to unacceptable signal to noise ratios in the far field remote from the transducer.

The present invention is based, inter alia, on the finding that such disadvantages may be mitigated or overcome by use of contrast agents comprising two or more types of gas-containing microparticles which differ in their resistance to ultrasound energy, i.e. in their susceptibility to ultrasonic pressure. Thus microparticle types having relatively low susceptibility to ultrasonic pressure will provide a response to high acoustic energy in the near field where microparticle types with relatively high susceptibility will tend to be inactivated through destruction. The more highly susceptible microparticle types will, however, be effective in the lower acoustic energy environment of the far field, where lower susceptibility microparticle types will tend to exhibit little interaction.

Thus according to one aspect of the present invention there is provided a combined preparation for simultaneous, separate or sequential use as an ultrasound contrast agent, said preparation comprising at least two different types of gas-containing microparticles, said microparticle types differing in their susceptibility to ultrasonic pressure.

According to a further feature of the invention there is provided a method of generating enhanced images of a human or non-human animal subject which comprises the steps of administering a contrast agent preparation as defined above to said subject and generating an ultrasound image of at least a part of said subject.

The differing susceptibility to ultrasonic pressure of the microparticle types may result from physical and/or chemical differences. Thus it may be possible to employ microparticle types which differ only in size, for example having a bimodal size distribution, in order to achieve the desired difference in susceptibility to ultrasonic pressure. More commonly, however, different encapsulating or other stabilising systems will be employed, for example comprising a first microparticle type which has relatively soft encapsulating shells and therefore has relatively high susceptibility to ultrasonic pressure and a second microparticle type which has relatively hard encapsulating or otherwise stabilising material, e.g. in shell or matrix form, and therefore has relatively low susceptibility to ultrasonic pressure.

The different microparticle types may be selected from any appropriate gas-containing microparticulate ultrasound contrast agents. Representative examples of such contrast agents include microbubbles of gas stabilised (e.g. at least partially encapsulated) by a coalescence-resistant surface membrane (for example gelatin, e.g. as described in WO-A-8002365), a filmogenic protein (for example an albumin such as human serum albumin, e.g. as described in U.S. Pat. No. 4,718,433, U.S. Pat. No. 4,774,958, U.S. Pat. No. 4,844,882, EP-A-0359246, WO-A-9112823, WO-A-9205806, WO-A-9217213, WO-A-9406477 or WO-A-9501187), a polymer material (for example a synthetic biodegradable polymer as described in EP-A-0398935, an elastic interfacial synthetic polymer membrane as described in EP-A-0458745, a microparticulate biodegradable polyaldehyde as described in EP-A-0441468, a microparticulate N-dicarboxylic acid derivative of a polyamino acid—polycyclic imide as described in EP-A-0458079, or a biodegradable polymer as described in WO-A-9317718 or WO-A-9607434), a non-polymeric and non-polymerisable wall-forming material (for example as described in WO-A-9521631), or a surfactant (for example a polyoxyethylenepolyoxypropylene block copolymer surfactant such as a Pluronic, a polymer surfactant as described in WO-A-9506518, or a film-forming surfactant such as a phospholipid, e.g. as described in WO-A-9211873, WO-A-9217212, WO-A-9222247, WO-A-9428780, or WO-A-9503835).

Other useful gas-containing microparticulate contrast agents include gas-containing solid systems, for example microparticles (especially aggregates of microparticles) having gas contained therewithin or otherwise associated therewith (for example being adsorbed on the surface thereof and/or contained within voids, cavities or pores therein, e.g. as described in EP-A-0122624, EP-A-0123235, EP-A-0365467, WO-A-9221382, WO-A-9300930, WO-A-9313802, WO-A-9313808 or WO-A-9313809). It will be appreciated that the echogenicity of such microparticulate contrast agents may derive directly from the contained/associated gas and/or from gas (e.g. microbubbles) liberated from the solid material (e.g. upon dissolution of the microparticulate structure).

The disclosure of all of the above-described documents relating to gas-containing contrast agent formulations are incorporated herein by reference.

Gas-containing microparticles preferably have an initial average size not exceeding 10 μm (e.g. of 7 μm or less) in order to permit their free passage through the pulmonary system following administration, e.g. by intravenous injection.

Where phospholipid-containing contrast agents are employed in accordance with the invention, e.g. in the form of gas microbubbles stabilised by monolayers, bilayers or multiple layers of one or more phospholipids, representative examples of useful phospholipids include lecithins (i.e. phosphatidylcholines), for example natural lecithins such as egg yolk lecithin or soya bean lecithin and synthetic or semisynthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; flurinated analogues of any of the foregoing; mixtures of any of the foregoing and mixtures with other lipids such as cholesterol. The fatty acyl groups of such phospholipids will typically each contain about 14–22 carbon atoms, for example as in palmitoyl and stearoyl groups. Lyso forms of such phospholipids are useful in accordance with the invention, the term "lyso" denoting phospholipids containing only one fatty acyl groups, this preferably being ester-linked to the 1-position carbon atom of the glyceryl moiety. Such lyso forms may advantageously be used in admixture with phospholipids containing two fatty acyl groups.

Phospholipid shells will in general tend to be relatively flexible, giving rise to microparticles with a relatively high susceptibility to ultrasonic pressure. The use of phospholipids predominantly (e.g. at least 75%) comprising molecules individually bearing net overall charge, e.g. negative charge, for example as in naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and/or cardiolipins, may be particularly advantageous.

Whilst we do not wish to be bound by theoretical considerations it is believed that electrostatic repulsion between charged phospholipid membranes encourages formation of stable and stabilising monolayers at microbubble-carrier liquid interfaces; the flexibility and deformability of such thin membranes enhances the echogenicity of such contrast agents, which are therefore preferred examples of microparticle types with relatively soft and flexible encapsulating shells.

Examples of microparticles comprising relatively hard and inflexible encapsulating shells include gas-containing polymer microparticles wherein the polymer is a biodegradable polymer containing units of formula (I)

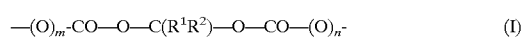

(where $R^1$ and $R^2$ each represent a hydrogen atom or a carbon-attached monovalent organic group or $R^1$ and $R^2$ together form a carbon-attached divalent organic group, and m and n are each zero or 1), e.g. as described in WO-A-9317718. Preferred examples of such microparticles comprise biodegradable polymers consisting of repeating units of formula (II)

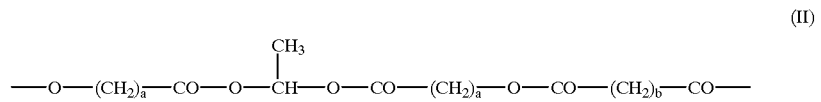

(where a represents an integer in the range 9–19, e.g. 13–17, and b represents an integer in the range 1–8, e.g. 3–6), as described in WO-A-9607434.

Contrast agents comprising gas microbubbles encapsulated by denatured and/or crosslinked protein (e.g. human serum albumin) shells, for example as described in WO-A-9217213 WO-A-9406477, may also be useful examples of microparticles with relatively hard encapsulating shells.

Other gas-containing microparticles which may be useful in contrast agents according to the invention include carbohydrates (for example hexoses such as glucose, fructose or galactose; disaccharides such as sucrose, lactose or maltose; pentoses such as arabinose, xylose or ribose; α-, β- and γ-cyclodextrins; polysaccharides such as starch, hydroxyethyl starch, amylose, amylopectin, glycogen, inulin, pulullan, dextran, carboxymethyl dextran, dextran phosphate, ketodextran, aminoethyldextran, alginates, chitin, chitosan, hyaluronic acid or heparin; and sugar alcohols, including alditols such as mannitol or sorbitol), inorganic salts (e.g. sodium chloride), organic salts (e.g. sodium citrate, sodium acetate or sodium tartrate), X-ray contrast agents (e.g. any of the commercially available carboxylic acid and non-ionic amide contrast agents typically containing at least one 2,4,6-triidophenyl group having a substituents such as carboxy, carbamoyl, N-alkylcarbamoyl, N-hydroxyalkylcarbamoyl, acylamino, N-alkylacylamino or acylaminomethyl at the 3- and/or 5-positions, as in metrizoic acid, diatrizoic acid, iothalamic acid, ioxaglic acid, iohexol, iopentol, iopamidol, iodixanol, iopromide, metrizamide, iodipamide, meglumine iodipamide, meglumine acetrizoate and meglumine diatrizoate), and polypeptides and proteins (e.g. gelatin or albumin such as human serum albumin).

In general, any biocompatible gas may be present in the microparticles, the term "gas" as used herein including any substances (including mixtures) substantially or completely in gaseous (including vapour) form at the normal human body temperature of 37° C. The gas may thus, for example, comprise air; nitrogen; oxygen; carbon dioxide; hydrogen; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example an alkane such as methane, ethane, a propane, a butane or a pentane, a cycloalkane such as cyclopropane, cyclobutane or cyclopentane, an alkene such as ethylene, propene, propadiene or a butene, or an alkyne such as acetylene or propyne; an ether such as dimethyl ether; a ketone; an ester; a halogenated low molecular weight hydrocarbon (e.g. containing up to 7 carbon atoms); or a mixture of any of the foregoing. Advantageously at least one of the halogen atoms in any halogenated gases is a fluorine atom; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons, e.g. perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes and perfluoropentanes, may be particularly advantageous in view of the recognised high stability in the bloodstream of microbubbles containing such gases.

The same or different gases may be employed in the different types of microparticles.

Contrast agent compositions and preparations in accordance with the invention may, for example, be prepared by appropriately admixing the different microparticle types. The microparticles and/or precursor forms thereof may be mixed in the dry state to give a product which may be formulated for administration by admixture with an appropriate aqueous carrier liquid such as sterile water for injection, or one or more of the microparticle types may be suspended or otherwise generated in an aqueous carrier liquid prior to such mixing. Aqueous preparations obtained in accordance with this latter embodiment may be used directly as contrast agents in accordance with the invention or may if desired be dried, for example by lyophilisation, to yield a storage-stable dried reconstitutable composition according to the invention.

Phospholipid-stabilised microbubble suspension for use in the above process may, for example, be prepared by generating a dispersion of gas microbubbles in an aqueous medium containing the phospholipid. This may, for example, be effected by subjecting the phospholipid-containing aqueous medium to any appropriate emulsion-generating technique, for example sonication, shaking, high pressure homogenisation, high speed stirring or high shear mixing, e.g. using a rotor-stator homogeniser, in the presence of the selected gas. The aqueous medium may, if desired, contain additives which serve as viscosity enhancers and/or as solubility aids for the lipid, such as alcohols or polyols, e.g. glycerol and/or propylene glycol.

The gas employed in the emulsification step need not be that desired in the final product. Thus most of this gas content may be removed during any subsequent lyophilisation step and residual gas may be removed by evacuation of the dried product, to which an atmosphere or overpressure of the desired end product gas may then be applied. The emulsification gas may therefore be selected purely to optimise the emulsification process parameters, without regard to end product considerations. Emulsification in the presence of a sulphur fluoride such as sulphur hexafluoride or a fluorinated low molecular weight hydrocarbon gas such as a perfluoroalkane or perfluorocycloalkane, preferably containing 4 or 5 carbon atoms, may be particularly advantageous in terms of ultimately yielding end products with consistent and narrowly distributed microbubble sizes.

The emulsification is conveniently effected at about ambient temperature, e.g. at ca. 25±10° C. It may be necessary initially to heat the aqueous medium to facilitate hydration and thus dispersion of the lipid and then allow it to equilibrate to ambient temperature prior to emulsification.

The resulting microbubble suspension may advantageously be subjected to one or more washing steps in order to separate and remove additives such as viscosity enhancers and solubility aids, as well as unwanted material such as non-gas-containing colloidal particles and undersized and/or oversized microbubbles. Such washing may be effected in per se known manner, the microbubbles being separated using techniques such as flotation or centrifugation. In this way size-fractionated microbubble dispersions may be prepared wherein at least 90% of the microbubbles have sizes within a 2 μm range, e.g. having a volume mean diameter within the range 2–5 μm.

Any lyophilisation step may advantageously be conducted in the presence of one or more cryoprotective and/or lyoprotective and/or bulking agents, such agent(s) advantageously being added after any washing steps, prior to lyophilisation. A substantial list of agents with cryoprotective and/or lyoprotective effects is given in Acta Pharm. Technol. 34(3), pp. 129–139 (1988), the contents of which are incorporated herein by reference. Examples of such agents include alcohols (e.g. aliphatic alcohols such as t-butanol), polyols such as glycerol, aminoacids such as glycine, carbohydrates (e.g. sugars such as sucrose, mannitol, trehalose, glucose, lactose and cyclodextrins, or polysaccharides such as dextran) and polyglycols such as polyethylene glycol, the use of physiologically well-tolerated sugars such as sucrose (e.g. in an amount such as to render the product isotonic or somewhat hypertonic) being preferred.

Since dried products will normally be reconstituted prior to administration, the mixed product may advantageously be filled into sealable vials prior to lyophilisation so as to give vials each containing an appropriate amount, e.g. a single dosage unit, of lyophilised dried product for reconstitution into an injectable form. By lyophilising the gas dispersion in individual vials rather than in bulk, handling of the lyophilised product and the risk of at least partially degrading its structure are avoided. Following lyophilisation and any optional further evacuation of gas and introduction into the headspace of gas desired to be present as microbubbles in the ultimately formulated contrast agent, the vials may be sealed with an appropriate closure.

In general the lyophilised dried product may be reconstituted by addition of an appropriate injectable carrier liquid such as sterile pyrogen-free water or saline for injection. Where the dried product is contained in a vial this is conveniently sealed with a septum through which the carrier liquid may be injected using a syringe. It may be advantageous to mix or gently shake the product following reconstitution; no more than gentle hand-shaking may be required to give reproducible products with consistent microbubbles size.

The following non-limitative Example serves to illustrate the invention.

EXAMPLE 1 a) Preparation of phospholipid-encapsulated perfluorobutane 500.4 mg hydrogenated egg phosphatidylserine was added to 100 ml water containing 5.4% (w/w) of a mixture of propylene glycol and glycerol (3:10 w/w). The mixture was shaken and heated to 80° C. for five minutes, allowed to cool to room temperature, shaken again and left standing overnight prior to use.

50 ml of the resulting solution was transferred to a round-bottomed flask with a conical neck. The flask was fitted with a glass jacket having a temperature control inlet and outlet connected to a water bath maintained at 25° C. A rotor stator mixing shaft was introduced into the solution and to avoid gas leakage the space between the neck wall and the mixing shaft was sealed with a specially designed metal plug fitted with an gas inlet/outlet connection for adjustment of gas content and pressure control. The gas outlet was connected to a vacuum pump and the solution was degassed for one minute. An atmosphere of perfluoro-n-butane gas was then applied through the gas inlet.

The solution was homogenised at 23000 rpm for 10 minutes, keeping the rotor stator mixing shaft such that the openings were slightly above the surface of the liquid. A white coloured creamy dispersion was obtained, which was transferred to a sealable container and flushed with perfluoro-n-butane. The dispersion was then transferred to a separating funnel and centrifuged at 12000 rpm for 30 minutes, yielding a creamy layer of bubbles at the top and a turbid infranatant. The infranatant was removed and replaced with water. The centrifugation was then repeated twice, but now at 12000 rpm for 15 minutes. After the last centrifugation, the supernatant was replaced by 10% (w/w) sucrose. 2 ml portions of the resulting dispersion were divided between 10 ml flat-bottomed vials specially designed for lyophilisation, and the vials were cooled to −47° C. and lyophilised for approximately 48 hours, giving a white fluffy solid substance. The vials were transferred to a vacuum chamber, and air was removed by a vacuum pump and replaced by perfluoro-n-butane gas.

b) Preparation of contrast agents comprising two microparticle types

Gas-containing polymer microparticles prepared in accordance with any of Examples 3(a)–(r) of WO-A-9607434 are added to vials containing the lyophilised product from Example 1(a) above, whereafter water for injection is added and the vials are gently hand-shaken for several seconds to give a contrast agent formulation according to the invention.

Alternatively water for injection is added to vials containing the lyophilised product from Example 1(a) above and the vials are gently hand-shaken to give microbubble dispersions to which the gas-containing polymer microparticles according to any of Examples 3(a)–(r) of WO-A-9607434 are added, either in dry form or as a dispersion in water for injection. The resulting mixture may be used directly as a contrast agent formulation in accordance with the invention or may be lyophilised to give a storage-stable dried product for subsequent reconstitution with an aqueous carrier such as water for injection.

EXAMPLE 2

In vivo imaging of dog heart

A 15 kg dog was anaesthetised with pentobarbital and kept in a supine position. Ultrasonic images of the heart were taken in a short axis view using an ATL HDI-3000 ultrasound apparatus with a P3-2 phased array transducer, designed for second harmonic imaging and operating with a transmit frequency of 1.6 MHz and a receive frequency of 3.2 MHz. A relatively high power (mechanical index 0.8) was used.

Two preparations for intravenous injection were used sequentially. Preparation A, from Example 1(a) above, consisted of "power-susceptible" microbubbles which were highly reflective to ultrasound but exhibited relatively low stability at high ultrasonic pressure. Preparation B, from Example 3(l) of WO-A-9607434, consisted of microparticles with higher stability at high ultrasonic pressure.

0.15 µl microbubbles/kg of Preparation A was initially injected into the dog. Imaging of the myocardium revealed enhancement of the anterior wall of the left ventricle by the contrast agent to be less than for the septum and the lateral wall, giving an inhomogeneity in the image which might be interpreted as a sign of abnormal perfusion.

A steady image was obtained approximately 1 minute after injection of Preparation A, whereupon 2.5 ml of a 10 mg/ml Preparation B suspension were injected. The observed enhancement of the anterior wall now increased and was better than for the septum and posterior wall, since Preparation B requires a high sound pressure to be efficacious as a contrast agent. Thus, whereas imaging with Preparation B alone would not give an overall image with sufficient quality for a good evaluation of all parts of the heart, the combined use of Preparations A and B revealed that the apparent perfusion defect observed with Preparation A alone was an artefact.

I claim:

1. A combined preparation for simultaneous, separate or sequential use as an ultrasound contrast agent, said contrast agent comprising a first gas-containing microparticle type which has relatively soft encapsulating shells comprising at least one phospholipid and a second gas-containing microparticle type which has relatively hard encapsulating or otherwise stabilising material selected from the group consisting of biodegradable polymers, denatured proteins, crosslinked proteins and denatured and crosslinked proteins, said two types of gas-containing microparticles each having an initial average size not exceeding 10 µm.

2. A preparation as claimed in claim 1 wherein said phospholipid shells comprise one or more phospholipids selected from phosphatidylcholines, phosphatidic acids, phosphatidylethanolamines, phosphatidylserines, phosphatidylglycerols, phosphatidylinositols, cardiolipins, sphingomyelins and fluorinated analogues of any of the following.

3. A preparation as claimed in claim 2 wherein at least 75% of said phospholipid shells comprise phospholipid molecules individually bearing net overall charge.

4. A preparation as claimed in claim 3 wherein at least 75% of said phospholipid shells comprise one or more syntheric or semisynthetic phosphatidylserines.

5. A preparation as claimed in claim 1 wherein the second gas-containing microparticle type comprises a biodegradable polymer consisting of repeating units of formula (II)

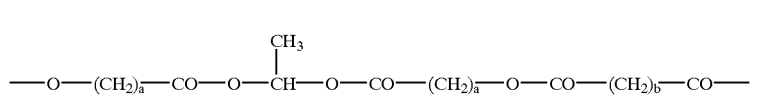

(II)

where a represents an integer in the range 9–19, and b represents an integer in the range 1–8.

6. A preparation as claimed in claim 5 wherein a represents an integer in the range 13–17 and b represents an integer in the range 3–6.

7. A preparation as claimed in claim 1 wherein said gas-containing microparticles comprise at least one gas selected from air, nitrogen, oxygen, carbon dioxide, hydrogen, noble gases, sulphur fluorides, selenium hexafluoride, optionally halogenated silanes, low molecular weight hydrocarbons, ethers, ketones, esters and halogenated low molecular weight hydrocarbons.

8. A preparation as claimed in claim 7 wherein at least one of the halogen atoms in any halogenated hydrocarbons is a fluorine atom.

9. A preparation as claimed in claim 7 wherein said gas is a perfluorinated low molecular weight hydrocarbon or sulphur hexafluoride.

10. A preparation as claimed in claim 1 wherein said first gas-containing microparticle type comprises a perfluorinated low molecular weight hydrocarbon or sulphur hexafluoride and said second gas-containing microparticle type comprises air.

11. A method of generating enhanced images of a human or non-human animal subject which comprises the steps of administering a preparation as claimed in claim 1 to said subject and generating an ultrasound image of at least a part of said subject.

* * * * *